United States Patent [19]

Kriesel

[11] Patent Number: 5,484,415
[45] Date of Patent: * Jan. 16, 1996

[54] FLUID DISPENSING APPARATUS

[75] Inventor: Marshall S. Kriesel, St. Paul, Minn.

[73] Assignee: Science Incorporated, Bloomington, Minn.

[*] Notice: The portion of the term of this patent subsequent to Jul. 18, 2012, has been disclaimed.

[21] Appl. No.: 192,031

[22] Filed: Feb. 3, 1994

Related U.S. Application Data

[63] Continuation-in-part of Ser. No. 156,685, Nov. 22, 1993, Pat. No. 5,433,709, which is a continuation-in-part of Ser. No. 53,723, Apr. 26, 1993, Pat. No. 5,354,278, which is a continuation-in-part of Ser. No. 870,521, Apr. 17, 1992, Pat. No. 5,263,940.

[51] Int. Cl.$^6$ ............................................. A61M 37/00
[52] U.S. Cl. .............................................................. 604/132
[58] Field of Search .................................. 604/132, 131, 604/93, 82–85, 92

[56] References Cited

U.S. PATENT DOCUMENTS

| 3,468,308 | 9/1969 | Bierman | 604/132 X |
|---|---|---|---|
| 3,469,578 | 9/1969 | Bierman . | |
| 4,386,929 | 6/1983 | Peery et al. | 604/132 |
| 4,419,096 | 12/1983 | Leeper et al. | 604/132 |
| 4,915,693 | 4/1990 | Hessel | 604/132 |
| 4,994,031 | 2/1991 | Theeuwes | 604/85 |
| 5,106,374 | 4/1992 | Apperson et al. | 604/131 X |
| 5,122,116 | 6/1992 | Kriesel et al. | 604/89 |
| 5,188,603 | 2/1993 | Vaillancourt | 604/131 |
| 5,199,604 | 4/1993 | Palmer et al. | 604/131 X |
| 5,263,940 | 11/1993 | Kriesel | 604/132 |
| 5,354,278 | 10/1994 | Kriesel | 604/132 |

Primary Examiner—Nicholas D. Lucchesi
Assistant Examiner—Jeffrey A. Smith
Attorney, Agent, or Firm—James E. Brunton

[57] ABSTRACT

An infusion apparatus for delivering beneficial agents, such as drugs to a patient at substantially a constant rate. The device uniquely includes a manifold system to which a plurality of elastomeric bladder type infusion devices are connected. Each infusion device includes an internally disposed functional substrate which carries the beneficial agent so that it can be mixed with the fluid as the fluid is being introduced into the device to distend the bladder to make it an energy source for controllably dispensing the solution mixture to the manifold system and thence to a patient. The manifold system includes control valves which permit fluid from selected infusion devices to be disposed from the apparatus.

17 Claims, 7 Drawing Sheets

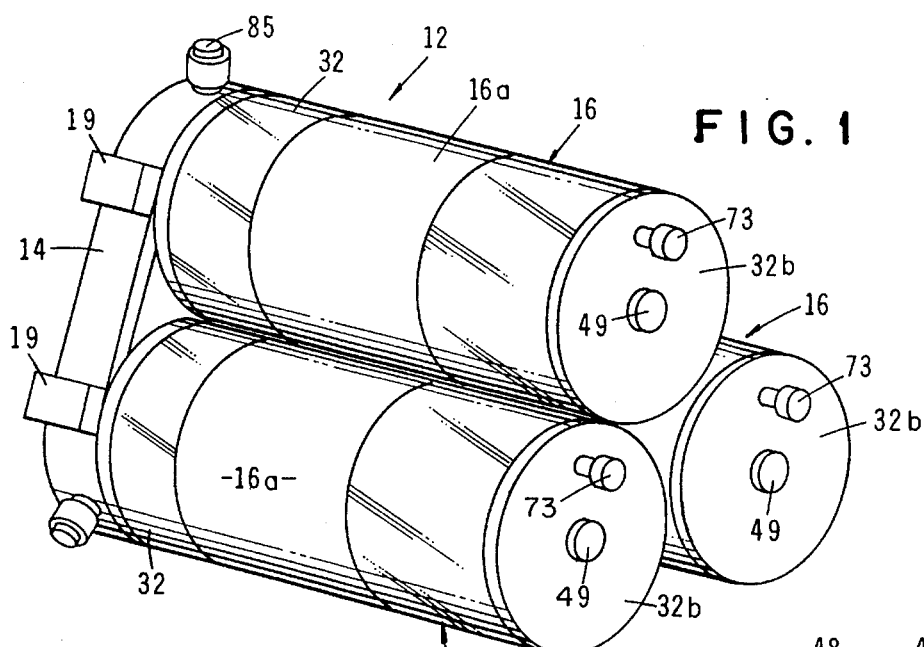
FIG. 1
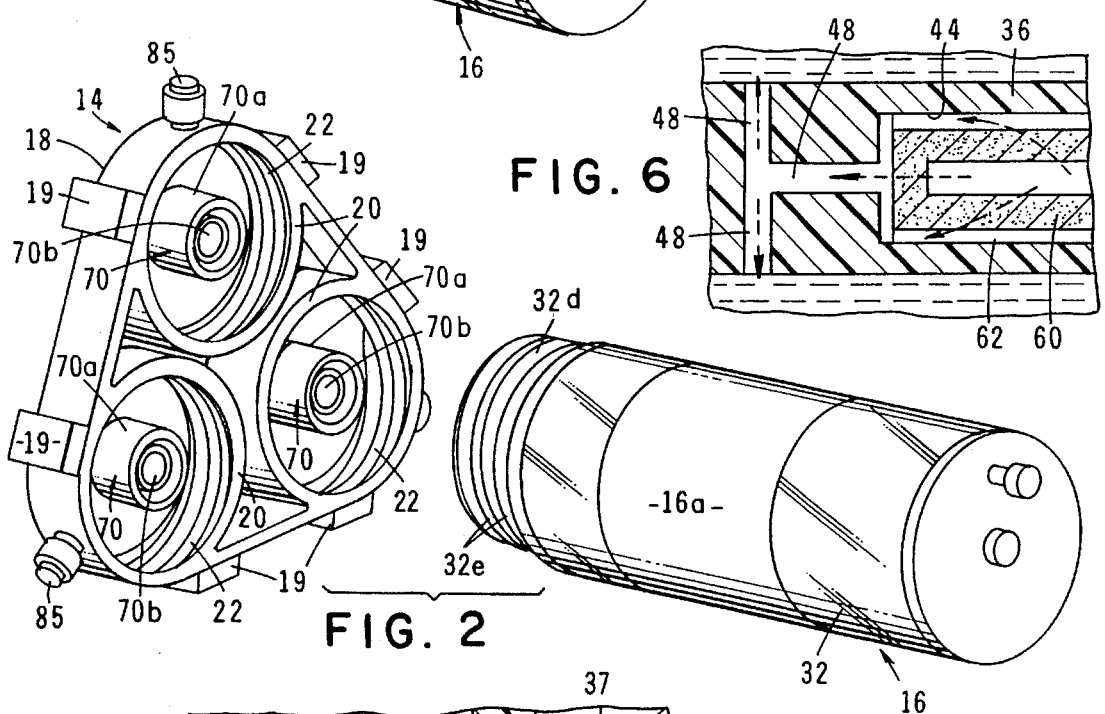
FIG. 2   FIG. 6
FIG. 5

FLUID DISPENSING APPARATUS

This is a Continuation-in-Part application of a U.S. application Ser. No. 08/156,685, filed on Nov. 22, 1993 entitled Fluid Dispenser (U.S. Pat. No. 5,433,709), which is a Continuation-in-Part of Ser. No. 08/053,723 filed Apr. 26, 1993 (U.S. Pat. No. 5,354,278), which is a Continuation-in-Part of application 07/870,521, filed on Apr. 17, 1992 (U.S. Pat. No. 5,263,940).

BACKGROUND OF THE INVENTION

1. Field of the Invention

The present invention relates generally to infusion devices. More particularly, the invention concerns an elastomeric bladder type infusion device which is used for delivering a beneficial agent to a patient at a substantially constant rate. The device uniquely includes means for intermixing a first compound, such as a drug, with a second component such as a parenteral liquid prior to delivering the solution thus formed to the patient.

2. Discussion of the Invention

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestesses the bladder in both the axial and radial directions when disposed therein, substantially filling the bladder in its unfilled state. The Hessel device also includes a one-way valve on the stress member which permits flow in the influent lumen only in the direction of the interior of the bladder.

Another type of balloon type infusion device is disclosed in U.S. Pat. No. 4,386,929 issued to Perry, et al. The Perry, et al. device has spaced apart inlet and outlet means and the bladder which is capable of expanding and contracting radially and axially upon inflation and deflation. When deflated the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated, before its subsequent inflation and deflation, substantially complete expulsion of the fluid contents of the bladder can be obtained.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time. In the device described in U.S. Pat. No. 3,469,578, the liquid is expelled solely by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tubelike member which is typically distendable both lengthwise and laterally when initially pressured. Admission and discharge of liquid is of necessity, through a single neck, or outlet portion of the balloon-like bladder.

None of the prior art devices known to applicant have the unique capability of the present invention for internally mixing a first compound, such as a drug, with a second compound such as a diluent, prior to expelling the beneficial agent thus formed from the device. Co-pending application, Ser. No. 08/053,723 describes in detail several embodiments of the invention and this last mentioned application is hereby incorporated by reference in its entirely as though fully set forth herein.

SUMMARY OF THE INVENTION

It is an object of the present invention to provide an elastomeric bladder stored energy type infusion device which can be filled with a fluid such as a diluent and which during filling efficiently mixes the diluent with an additive such as a drug or other type of beneficial agent.

More particularly, it is an object of the invention to provide an infusion device of the aforementioned character which provides the opportunity to add to the diluent or other parenteral fluid being introduced into the device selected elements, chemical compounds and biologically active materials such as drugs, medicaments, biological agents, or other therapeutic agents (additives). This addition is accomplished by removably affixing the selected additives to various forms of support structures which can be placed within the path of the fluid flowing through the device. In this way, the delivery system of the invention can be safely rendered therapeutically active upon solution of the additive with the selected parenteral fluid.

A primary object of the present invention, as more fully described in the paragraphs which follow, is to provide a novel manifold system to which several elastomeric bladder type infusion devices of the class described in Ser. No. 08/053,723 can be operably interconnected.

Another object of the invention is to provide an apparatus which can be factory prefilled with a wide variety of medicinal fluid or one which can readily be filled in the field shortly prior to use.

Other objects of the invention are set forth in Ser. No. 08/053,723 which is incorporated herein by reference.

By way of summary description, the novel apparatus of the present invention permits the controlled delivery from the apparatus of large volumes of the same or different fluids at controlled rates in accordance with a predetermined delivery regimen. Although each of the individual fluid dispensers of the apparatus can be of varying reservoir volumes, by interconnecting a plurality of dispensers to the unique manifolding system of the invention, the controlled delivery over a given protocol of a substantial volume of fluids can readily be accomplished. The individual fluid dispensers of selected volumes are interconnected with the manifolding system by attaching the dispensers to an easily portable mounting base upon which the manifolding system is mounted. A convenient valving system permits the dispensers to be opened to the manifold system in any sequence that may be desired. The outlet port of the manifolding system is, in turn, coupled with an infusion set or other fluid transfer means for controllably transferring the fluid from the delivery apparatus to a patient, or to any other remote site.

In one form of the apparatus of the present invention, three fluid dispensers, each having an internal stored energy source, can be conveniently mounted on a portable mounting base. Filling means, which also comprises a part of the apparatus of the invention, can be used to fill, or charge, the reservoirs of the mounted fluid dispensers with any selected fluid such as a diluent or with any of a variety of beneficial agents. Through the use of the novel apparatus of the invention, multiple agents can be dispensed over time individually or in cooperation with a diluent.

BRIEF DESCRIPTION OF THE DRAWINGS

FIG. 1 is a generally perspective view of the fluid delivery device of one form of the present invention.

FIG. 2 is a generally perspective, exploded view of the device shown in FIG. 1 with one dispenser shown in a manifold connection position.

FIG. 5 is an enlarged, cross-sectional view taken along lines 5—5 of FIG. 4.

FIG. 6 is an enlarged, cross-sectional view of the area 6 indicated in FIG. 4.

FIG. 11 is a cross-sectional view of the dispenser of

FIG. 10 shown coupled with a manifold of the character shown in FIG. 2.

DESCRIPTION OF ONE FORM OF THE INVENTION

Figure 3:
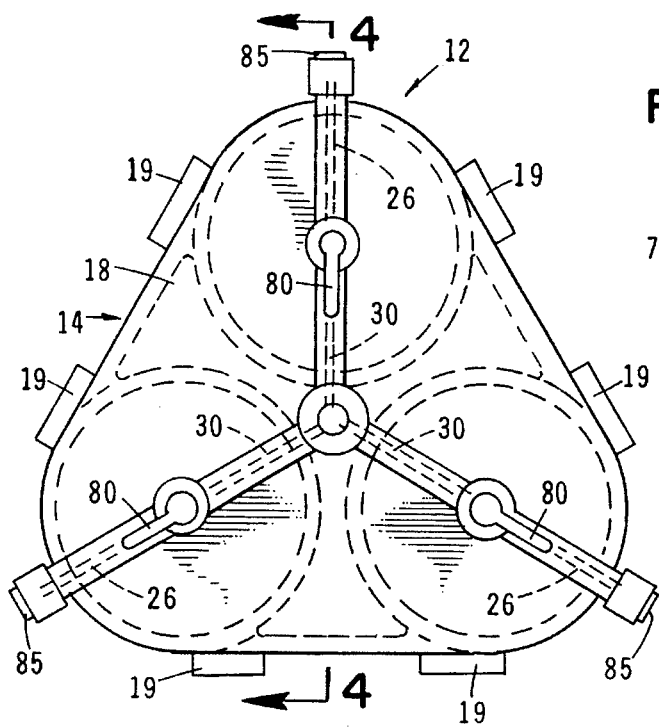
FIG. 3 is an end view of the apparatus of FIG. 1.
Figure 4:
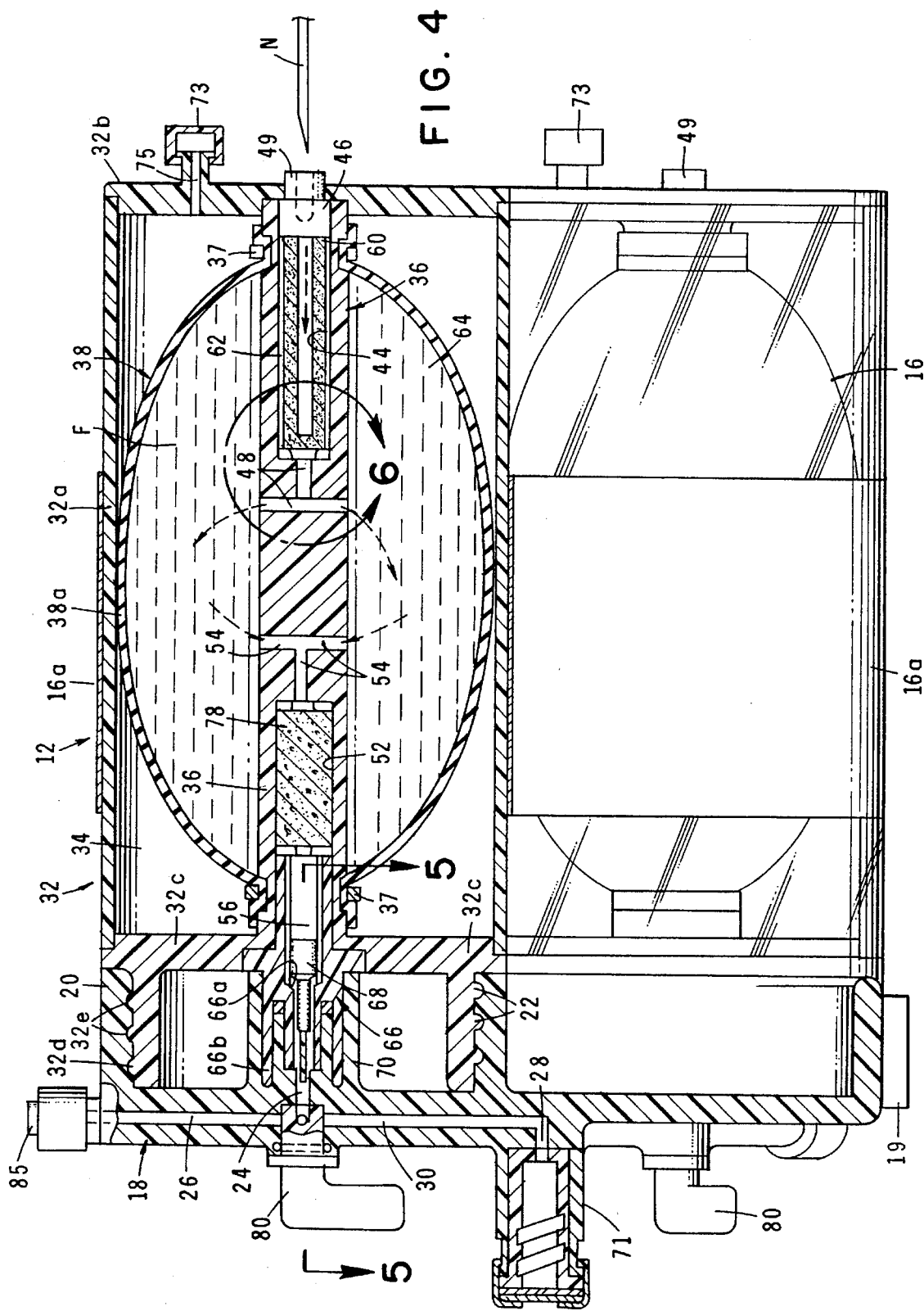
FIG. 4 is an enlarged view taken along lines 4—4 of FIG. 3.

Referring to the drawings and particularly to FIGS. 1, 2, and 3, the apparatus of one form of the invention is there illustrated and generally identified by a numeral 12. The apparatus comprises a portable mounting base assembly 14 to which a plurality of fluid dispensers 16 can be interconnected. As best seen in FIGS. 2 and 4, the mounting base assembly 14 comprises a generally triangular shaped planar base wall 18 having a plurality of generally circular shaped, upstanding connector walls 20 connected thereto. As shown in FIG. 2, each of the connector walls 20 is provided with internal threads. Base wall 18 is provided with a plurality of first and second inlet passageways 24 and 26 which communicate with an outlet passageway 28 via a plurality of connector passageways 30 (FIG. 3). Valve means, which are of a character presently to be described, are in communication with outlet passageway 28 and function to control the flow of fluid from passageways 24 and 26 toward outlet passageway 28. A plurality of supporting feet 19 are provided along the periphery of base wall 18.

In the form of the invention shown in FIGS. 1 through 6, three fluid dispensers 16 are connected to mounting base assembly 14. Each fluid dispenser 16 comprises an elongated housing 32 having an internal chamber 34, a support 36 disposed within internal chamber 34 and extending longitudinally of the housing 32, and a generally cylindrically shaped, elongated elastomeric member 38. A medicament label 16a is provided on each fluid dispenser 16.

Housing 32 comprises a cylindrically shaped central portion 32a and inlet and outlet end plates 32b and 32c respectively. Central section 32a and end plates 32b and 32c may be constructed of any suitable rigid plastic material such as a polycarbonate and end plates 32b and 32c can be affixed to the central section by any suitable means such as adhesive bonding or an appropriate sonic weldment. Elastomeric member 38 is securely affixed proximate its ends to support 36 by means of suitable ring clamps 37 such as self-locking plastic panduit strips.

As best seen by referring to FIG. 4, support 36 is provided with a first chamber 44 having a fluid inlet 46 and a fluid outlet 48 (see also FIG. 6). Fluid inlet 46 is accessible via filling means here shown as a septum 49. Septum 49 can be constructed from a self-sealing, non-coring material such as silicone SEBS, which can be sealably punctured by a needle of a conventional syringe, or may be provided with a slit adapted to accept a blunt cannula of a character well know to those skilled in the art. Septum 49 is receivable within one end of chamber 44 and extends through end wall 32b of housing 32 in the manner shown in FIG. 4. Support 36 is also provided with a second chamber 52 having fluid passageways 54 and an outlet fluid passageway 56. It is to be observed that elastomeric member 38 includes a central portion generally designated as 38a which overlays fluid outlet passageway 48 and fluid inlet passageways 54 of support 36.

As discussed in detail in co-pending Ser. No. 08/053,723, which is incorporated hereby by reference, the dispensing device of the invention is unique in that it provides an opportunity to add to a diluent or other parenteral fluid that is introduced into the device via septum 49, selected elements, chemical compounds and biologically active materials such as drugs, medicaments, biological agents and other therapeutic agents (additives). This addition is accomplished by removably affixing selecting additives to various forms of support structures which can be placed into chamber 44 of support member 36 so that they reside within the path of the fluid flowing through inlet fluid passageway 46 and outlet passageway 48 of support member 36. Reference should be made to Ser. No. 08/053,723 for the definition of the following terms: Element; Additive; Beneficial Agents; Biologically Active Materials; Adding Means, and Additive Presentation Means.

In using the apparatus of the invention, septum or non-coring injection site 49 is penetrated by needle "N" of a syringe (FIG. 4) and a parenteral fluid, such as a sterile diluent, is introduced into inlet passageway 46 using the needle syringe. As indicated by the arrows in FIG. 4, as the diluent flows longitudinally of inlet passageway 46 it will pass through porous member 60, into flow channels 62 which surround member or substrate 60 and then into fluid reservoir 64 (FIG. 4) via outlet passageway 48. This diluent flow under pressure will urge bladder 38 outwardly into the position shown in FIG. 4 and, in so doing, will impart internal stresses which tend to continuously urge the bladder toward a less distended configuration.

As the liquid flow through porous member 60, the additives presented to the liquid will be releasably separated from the member and added to the flow, or solubilized by the diluent, thereby activating the diluent to form the therapeutic solution to be dispensed to the patient.

The various types of parenteral fluid and the numerous forms of adding means or additive assemblies illustrated and described in Ser. No. 08/053,723 can readily be used in the apparatus of the present invention. These various fluids and adding means are intended to merely exemplify, not to limit, the wide variety of materials, constructions and techniques for affinity and separation that can be used to introduce the desired additives into the liquid introduced into the inlet flow passageway 46 of the device via septum 49.

After the diluent or other parenteral fluid is introduced into the fluid dispensers and mixed with the additive contained therein, the fluid dispensers can be interconnected with portable mounting base assembly 14 in the manner shown in FIGS. 1 and 2. In this regard it is to be noted that wall 32c of each of the dispenser housings 32 is provided with an outwardly extending wall 32d having external threads 32e. Threads 32e are mateable with threads 22 provided on the mounting base so that the fluid dispensers can be readily coupled with the mounting base to form the construction shown in FIG. 4.

As best seen in FIGS. 4 and 5, support member valve means are provided on forward wall 32c of each fluid dispenser 16 for controlling the flow of fluid between outlet passageway 56 of the dispenser and one of the first inlet passageway 24 of the mounting base assembly. This valve means here comprises a valve body 66, which is connected to wall 32c and extends outwardly therefrom, and a valve member 68, which is reciprocally movable within body 66. Body 66 is provided with a valve seat 66a which is sealably engaged by valve member 68 when the member is in a first closed position.

Referring to FIGS. 2 and 5, in order to permit precise coupling of the fluid dispensers with the mounting base, wall 18 is provided with a plurality of upstanding, socket like protuberances 70 which closely receive valve bodies 66 of the fluid dispensers. Protuberances 70 comprise a part of the support member valve operating means of the invention and each includes an outer, generally cylindrical wall 70a and an inner concentric, cylindrical wall 70b within which is mounted a valve operating stem 72 (FIG. 5). Stem 72 engages valve member 68 as each fluid dispenser is threadably coupled with the mounting base assembly and, as shown in FIG. 5, moves valve member 68 into a second valve open position, thereby permitting fluid flow from outlet passageway 56 into inlet passageway 24 of the mounting base. To guide movement of the valve body into the socket-like protuberance 70, each valve body includes a skirt-like portion 66b which is closely received between cylindrical walls 70a and 70b of the protuberances 70.

After each fluid dispenser is coupled with the base assembly so that each valve member 68 is in the open position shown in FIG. 4, fluid can be transferred to the mounting base assembly and then to a patient or to a remote site via a transfer tube (not shown) which is appropriately connected to a connector 71, provided on base wall 18. Connector 71 can be a luer connector or any other suitable connector of a character well known in the art. The fluid transfer step is accomplished by first removing the protective caps 73 which cover the venting ports 75 which are provided in each end wall 32b and then by selectively opening one or more of the mounting base valve means, or rotating control valves 80, which are mounted on base wall 18. As best seen in FIG. 4, control valves 80 are disposed intermediate first and second inlet passageways 24 and 26 and outlet passageway 28 and function to control the flow of fluid toward the outlet passageway.

Upon opening a selected one of the control valves 80, the bladder 38 of the dispenser associated with that control valve will move toward its less distended, initial starting position thereby urging the fluid "F" contained within reservoir of that dispenser through passageways 54 of the support 36. The fluid "F" which is now the diluent mixed with the additive, will flow into chamber 52 and through a flow a rate control means shown here as a porous rate control filter 78. Filter 78 can be constructed from a porous ceramic or other suitable porous plastic material such as polysulfone and can be provided with the desired porosity in a manner well known to those skilled in the art.

Fluid flowing through filter 78 will next flow into passageway 56, past valve member 68 and into inlet passageway 24 of the mounting base assembly which is associated with the open control valve 80. Next, the fluid will flow past the control valve 80 and into the associated passageway 30 and thence into outlet passageway 28. From passageway 28, the fluid will flow through connector 71 and outwardly of the apparatus.

Fluid can also be introduced into the mounting base assembly via auxiliary septums 85 mounted on base wall 18 and in communication with second inlet passageways 26. Septums 85 can be constructed from a self-sealing, non-coring material such as silicone SEBS, which can be sealably punctured by a needle of a conventional syringe or they may be provided with a slit adapted to accept a blunt cannula of a character well known to those skilled in the art. By appropriate operation of control valves 80, fluid added via septums 85 can be intermixed with fluid flowing into the mounting base from the fluid dispensers or it can flow directly to outlet passageway 28 via connector passageways 30. The fluid added via septums 85 can be a diluent or any type of beneficial agent of the character defined in Ser. No. 08/053,723.

Figure 9:
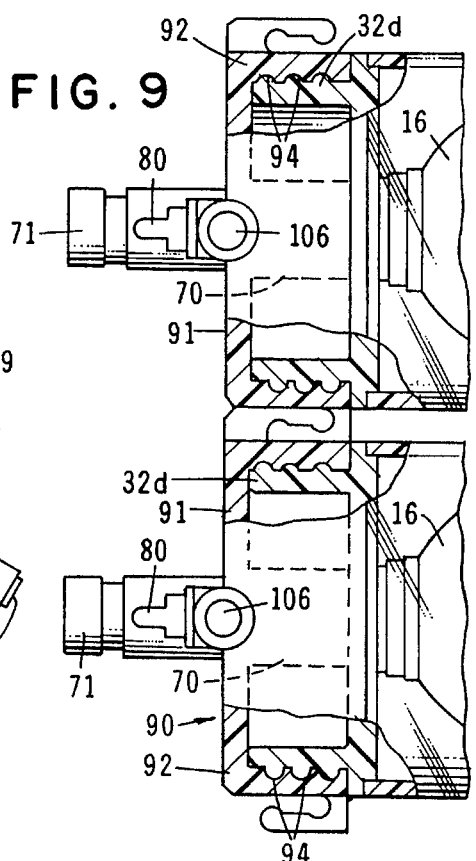
FIG. 9 is a cross-sectional view taken along lines 9—9 of FIG. 8.
Figure 7:
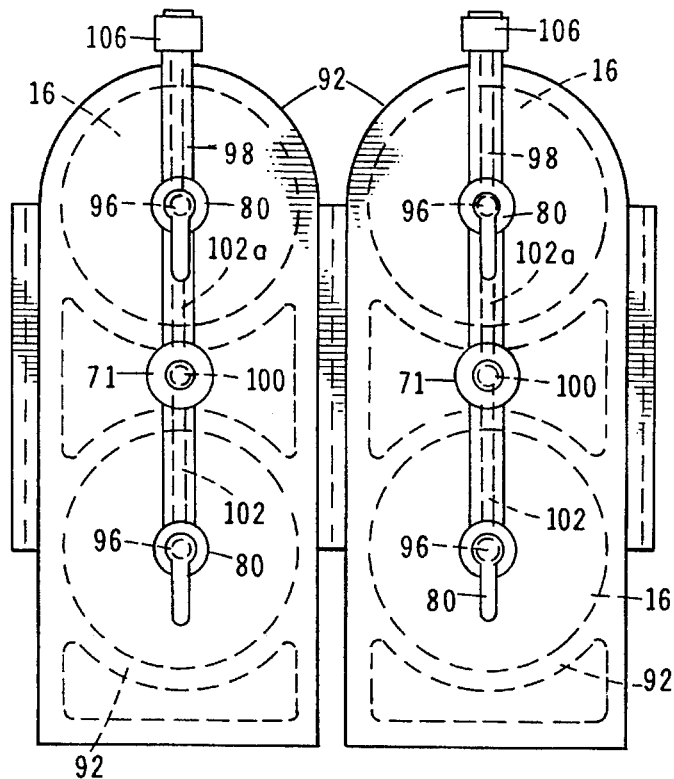
FIG. 7 is an end view of an alternate embodiment of the invention.
Figure 8:
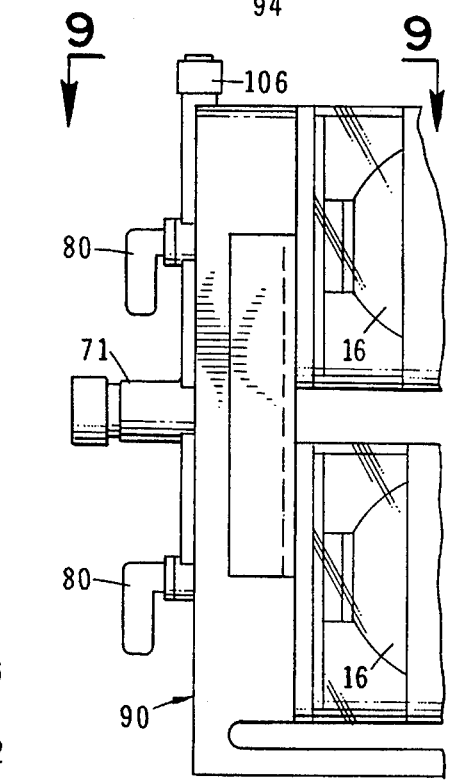
FIG. 8 is a fragmentary, side-elevational view of the apparatus shown in FIG. 7.

Referring now to FIGS. 7 through 9, another form of the invention is there shown. This form of the invention is similar in many respects to that previously described herein and like numerals are used to identify like components. More particularly, the fluid dispensers 16 are of identical construction to those shown in FIGS. 1 through 6. However, in this latest form of the invention, the mounting base assembly is constructed to accept four dispensing units 16.

In this alternate embodiment of the invention, the mounting base assembly 90 includes a generally rectangular planar base wall 91 having a plurality of generally circular shaped, upstanding connector walls 92 connected thereto. As shown in FIG. 9, each of the connector walls 92 is provided with internal threads 94. As before, base wall 90 is provided with first and second inlet passageways 96 and 98 which communicate with a pair of outlet passageways 100 via a plurality of connector passageways 102 (FIG. 7). Valve means, which are of a character previously described, are in communication with outlet passageways 100 and function to control the flow of fluid from passageways 96 and 98 toward outlet passageways 100.

In the form of the invention shown in FIGS. 7 through 9, four fluid dispensers 16 of the character previously described are connected to mounting base assembly 90.

As before, base wall 91 is provided with a plurality of upstanding, socket like protuberances 70 which closely receive valve bodies 66 of the fluid dispensers. Protuberances 70 comprise a part of the support member valve operating means of the invention and each includes a valve operating stem 72 of the character previously described. Stem 72 engages valve member 68 as each fluid dispenser is threadably coupled with the mounting base assembly and, as before moves valve member 68 into a second valve open position thereby permitting fluid flow from outlet passageway 56 thereof into one of the inlet passageways 96 of the mounting base.

After each fluid dispenser is coupled with the base assembly so that each valve member 68 is in the open position, fluid can be transferred to the mounting base assembly 90 and then to a patient or to a remote site via a transfer tube (not shown) which is appropriately connected to one of two connectors 71, provided on base wall 91. The fluid transfer step is accomplished as before by first removing the protective caps 73 which cover the venting ports 75 which are provided in each end wall 32b and then by selectively opening one or more of the mounting base valve means, or rotating control valves 80, which are mounted on base wall 91. As best seen in FIG. 7, control valves 80 are disposed intermediate first and second inlet passageways 96 and 98 and outlet passageway 100 and function to control the flow of fluid toward the outlet passageway.

Upon opening a selected one of the control valves 80, the bladder 38 of the dispenser associated with that control valve will move toward its less distended, initial starting position thereby urging the fluid "F" contained within reservoir of that dispenser outwardly of the apparatus in the manner previously described.

Fluid can also be introduced into mounting base assembly 90 via anxillary septums 106 carried by the base assembly and in communication with second inlet passageways 98. Septums 106 can be constructed from a self-sealing, noncoring material such as silicone SEBS, which can be sealably punctured by a needle of a conventional syringe or they may be provided with a slit adapted to accept a blunt cannula of a character well known to those skilled in the art. By appropriate operation of control valves 80, fluid added via septums 106 can be intermixed with fluid flowing into the mounting base from the fluid dispensers or it can flow directly to outlet passageway 100 via connector passageways 102 identified in FIG. 7 as 102a.

The materials used in the construction of the fluid dispensers 16 is discussed in detail in Ser. No. 08/053,723. The material used in the construction of mounting base assemblies 14 and 90 can be polycarbonate or any suitable rigid material with characteristics similar to polycarbonate.

Figure 10:
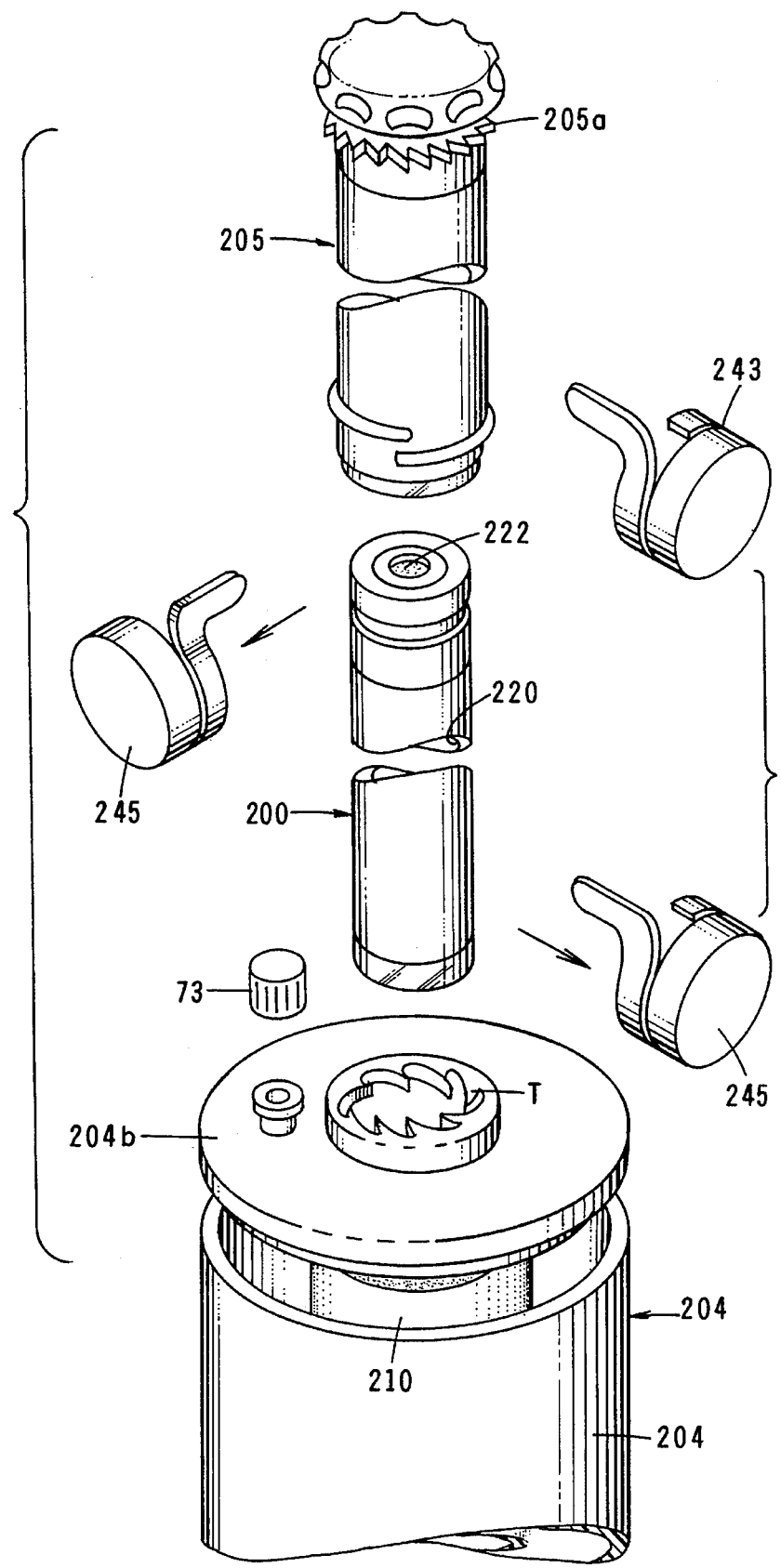
FIG. 10 is a fragmentary, generally perspective, exploded view of an alternate form of dispenser of the invention usable with a manifold of the character shown in FIG. 2.
Figure 11:
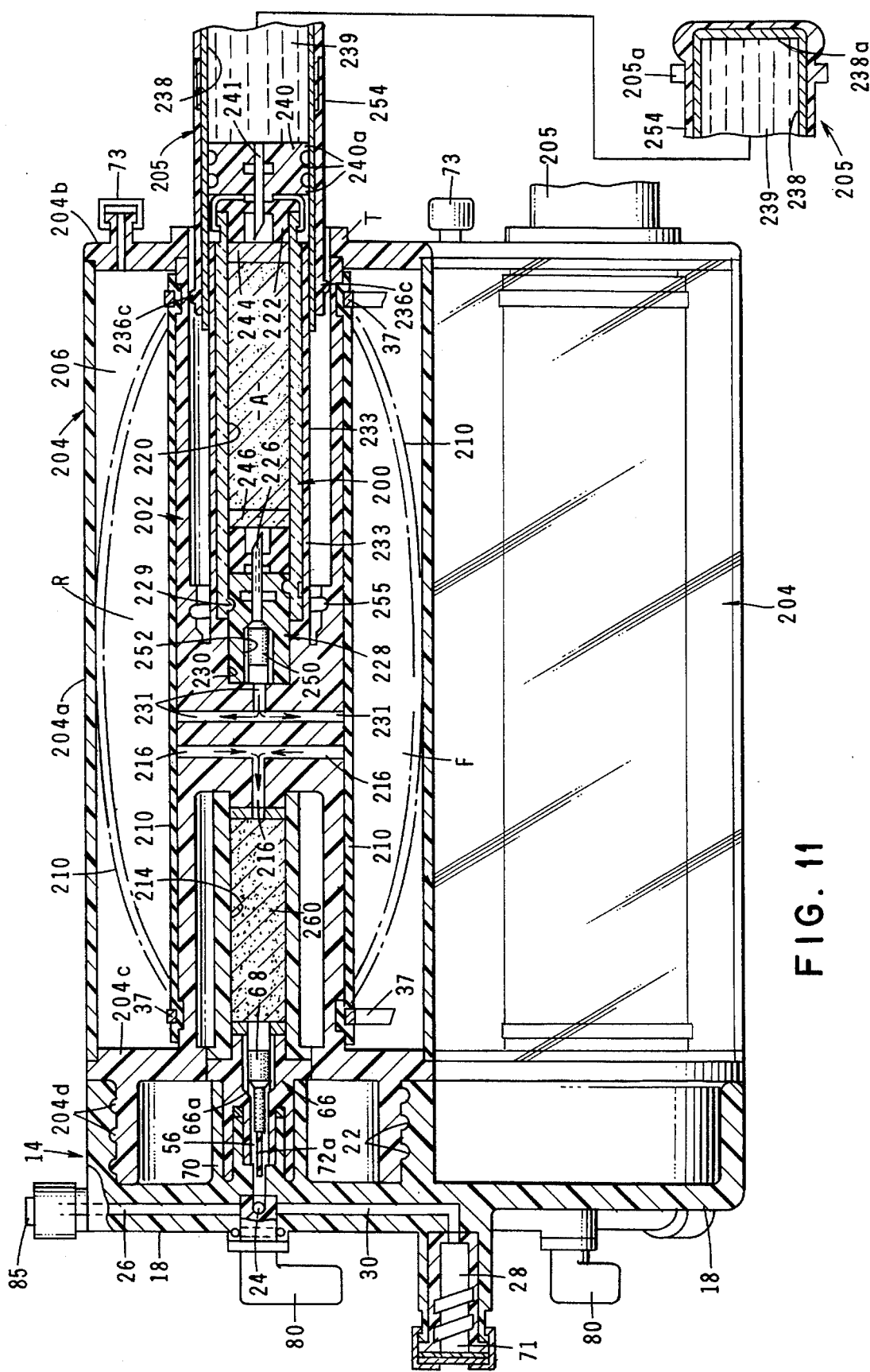

Turning now to FIGS. 10 and 11, still another form of the dispenser of the apparatus of the invention is there shown. The apparatus is quite similar to that previously described and like numerals have been used to identify like components. More particularly, the drug vial or additive assemblage 200 of this embodiment is identical to that identified by the numeral 318 in Ser. No. 08/053,723 and shown in FIG. 24 of that application. In using the apparatus of this latest form of the invention, which embodies vial 200, the vial is first secured within the inlet chamber 203 of the central support 202 of the dispensing device 204 as shown in FIG. 11. Next, fluid is introduced into the device to charge the reservoir thereof by means of a separate cooperating diluent assembly 205.

As best seen in FIG. 11, dispensing device 204 of this form of the invention comprises a cylindrically shaped central portion 204a to which end plates 204b and 204c are connected to define an internal chamber 206. Support means which includes elongated support 202 is disposed within chamber 206 and extends longitudinally thereof. As before an elastomeric member 210 is connected to support 202 by suitable clamps 37.

As best seen in FIG. 11, support 202 is provided with an outlet chamber 214 and includes fluid passageways 216 leading to reservoir "R". In communication with chamber 214 is support valve means of the character shown in FIG. 2 and, as previously described, comprises a valve body 66 and a reciprocating valve member 68. Body 66 is provided with a valve seat 66a which is sealably engaged by valve member 68 when the valve member is in a first closed position. Receivable within outlet chamber 214 is a filter means for filtering fluid flowing from reservoir "R" toward the dispensing means.

The additive assembly 200 of the adding means of this latest form of the invention includes a chamber 220 which is sealed at either end by septums 222 and 224. As before, the septums can be constructed from a self-sealing, noncoring material such as silicone SEBS which can be sealably punctured by a hollow needle such as needle 226 which is mounted in a valve housing 228 carried within a chamber 230 provided in support 202. It is to be noted that the additive assembly is internally threaded while the valve housing 228 is provided with a mating thread. With this construction, as the additive assembly 200 is inserted into the inlet chamber 203 of the support 202 and is moved into a seated position, needle 226 will pierce septum 224 in the manner shown in FIG. 11. This opens fluid communication between the internal chamber 220 of the additive assembly and the reservoir "R" via passageways 231.

Receivable over a tubular wall 233 of support 202 within which additive assembly 200 is received is the diluent container 205a. Container 205a, which may be a glass vial, includes a fluid reservoir 238 for containing the liquid component or parenteral fluid 239 as defined herein. During the charging and mixing step, fluid container assembly 205 is telescopically receivable over wall 233 in the manner shown in FIG. 11. In the present form of the invention, reservoir 238 of the container is closed by a piston 240 which is telescopically movable within fluid reservoir 238 from a first position shown in FIG. 11 to a second position wherein the piston is disposed proximate the closed end of the container. Piston 240 is provided with a plurality of circumferentially extending sealing beads 240a which sealably engage the inner walls of container 205a as the piston moves inwardly of reservoir 238. Affixed to piston 240 is an outwardly protruding hollow needle 241, the purpose of which will presently be discussed. During storage, a tear-away-type removable cover 243 (FIG. 10) encapsulates the forward face of piston 240 and sealably closes the inboard end of the fluid container. After container 205 has been filled with a suitable first component, such as parenteral fluid 239, piston 240 is inserted into the open end of the container and the sealing cap is emplaced over the assemblage thus formed so as to maintain the first component, such as a diluent, in a sterile, sealed condition until time of use.

In using the apparatus of this latest form of the invention, closure caps 245, which are provided at either end of the additive assembly, are first removed and vent cap 73 of dispenser 204 is also removed. The additive assembly is then inserted into the open end of chamber 203 and is threadably mated with valve support member 228 which includes a circumferential groove 229. As the additive subassembly mates with member 228, hollow needle 226 will penetrate septum 224 of the assembly in the manner shown in FIG. 11. (See also FIG. 25 of Ser. No. 08/053,723).

With the additive assembly positioned within central support 202 in the manner shown in FIG. 11, the tear-away cap 243 of the fluid container assembly 205 is removed and the container is emplaced over tubular wall 233 which surrounds the additive assembly. As the container assembly is urged to the left as viewed in FIG. 11, needle 241 will pierce septum 222 of the additive assembly opening a fluid path between reservoir 238 of the fluid container and the interior chamber 220 of the additive assembly. Continued inward telescopic movement of the fluid container will cause piston 240 to move inwardly of the fluid container forcing the diluent 239 contained therewithin through hollow needle 241, through porous glass frit 244 and then around, about and through the additive "A" disposed within chamber 220. The fluid mixture thus formed will flow through an inboard glass frit 246 and into hollow needle 226 causing a valve member 250, which is carried within a cavity 252 provided in member 228, to move to the left or open position. This, in turn, will permit the fluid mixture to flow into circumferentially spaced fluid passageways provided in member 238 (FIG. 25A) of Ser. No. 08/053,723 and then into passageways 231 formed in support 202. The fluid flowing through passageways 231 will pressurally engage elastomeric member 210 causing it to distend outwardly in the manner shown by the phantom lines in FIG. 11.

When piston 240 of the diluent container reaches the end 238a of reservoir 238 (FIG. 11), a thread 236c, which is provided on the exterior surface 236 of an outer wrap 254 which surrounds of container 205, will move into threaded engagement with an internal thread 255 provided within chamber 203 of support 202. Continued rotation of fluid container 205 will then cause tabs 205a provided on the container to lockably engage teeth "T" provided on end plate 204b thereby preventing removal of the container assembly from the dispensing device.

After the diluent or other parenteral fluid is introduced into the fluid dispensers and mixed with the additive contained therein, the fluid dispensers can be interconnected with portable mounting base assembly 14 in the manner shown in FIG. 11. In this regard it is to be noted that the mounting assembly 14 is of identical construction to that previously described herein so that external threads 204d provided on each dispenser housing 204 are mateable with threads 22 provided on the mounting base so that the fluid dispensers can be readily coupled with the mounting base to form the assemblage shown in FIG. 11.

As before, in order to permit precise coupling of the fluid dispensers with the mounting base, wall 18 thereof is provided with a plurality of upstanding, socket like protuberances 70 which closely receive valve bodies 66 of the fluid dispensers. As each fluid dispenser is threadably coupled with the mounting base assembly, stem 72a moves valve member 68 into a second valve open position, thereby permitting fluid flow from outlet passageway 56 into inlet passageway 24 of the mounting base.

After each fluid dispenser is coupled with the base assembly so that each valve member 68 is in the open position shown in FIG. 11, fluid can be transferred to the mounting base assembly and then to a patient or to a remote site in the same manner as previously described herein. Upon opening a selected one of the control valves 80, the bladder 210 of the dispenser associated with that control valve will move toward its less distended, initial starting position thereby urging the fluid "F" contained within reservoir of that dispenser through passageways 216 of the support 202 The fluid "F" which is now the diluent mixed with the additive, will flow into chamber 214 and through a filter means shown here as a porous rate control filter 260. Filter 260 can be constructed from a porous ceramic or other suitable porous plastic material such as polysulfone and can be provided with the desired porosity in a manner well known to those skilled in the art.

Fluid flowing through filter 260, will next flow into passageway 56, past open valve member 68 and into inlet passageway 24 of the mounting base assembly which is associated with the open control valve 80. Next, the fluid will flow past the control valve 80 and into the associated passageway 30 and thence into outlet passageway 28. From passageway 28, the fluid will flow through connector 71 and outwardly of the apparatus in the manner previously discussed.

As in the earlier described embodiments, fluid can also be introduced into the mounting base assembly via auxiliary septums 85 which are mounted on base wall 18 and which are in communication with second inlet passageways 26. Septums 85 can be constructed from a self-sealing, non-coring material such as silicone SEBS, which can be sealably punctured by a needle of a conventional syringe or they may be provided with a slit adapted to accept a blunt cannula of a character well known to those skilled in the art. By appropriate operation of control valves 80, fluid added via septums 85 can be intermixed with fluid flowing into the mounting base from the fluid dispensers or it can flow directly to outlet passageway 28 via connector passageways 30. The fluid added via septums 85 can be a diluent or any type of beneficial agent of the character defined in Ser. No. 08/053,723.

Figure 12:
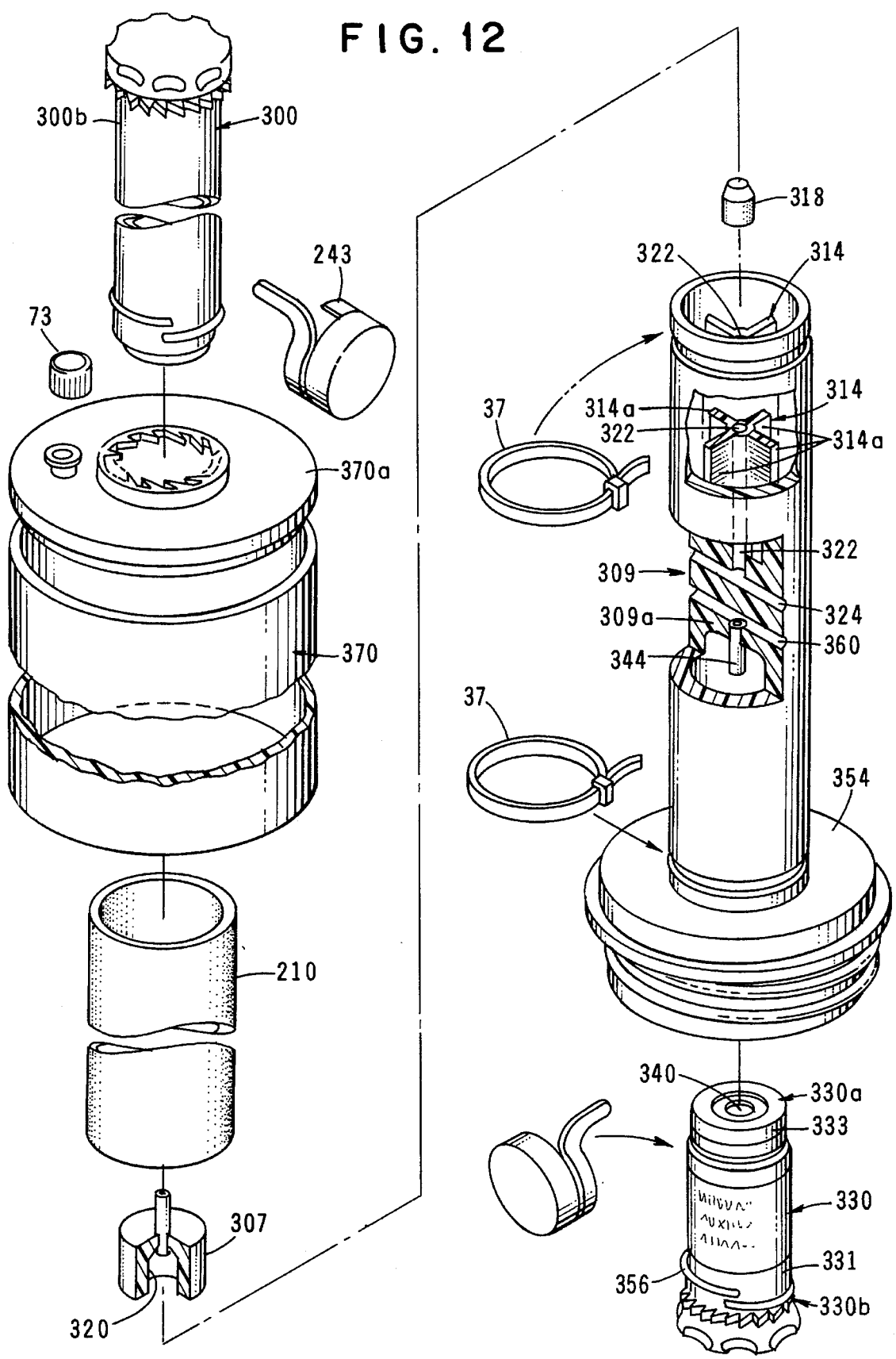
FIG. 12 is a generally perspective, exploded view of still another form of the dispenser of the invention.
Figure 13:
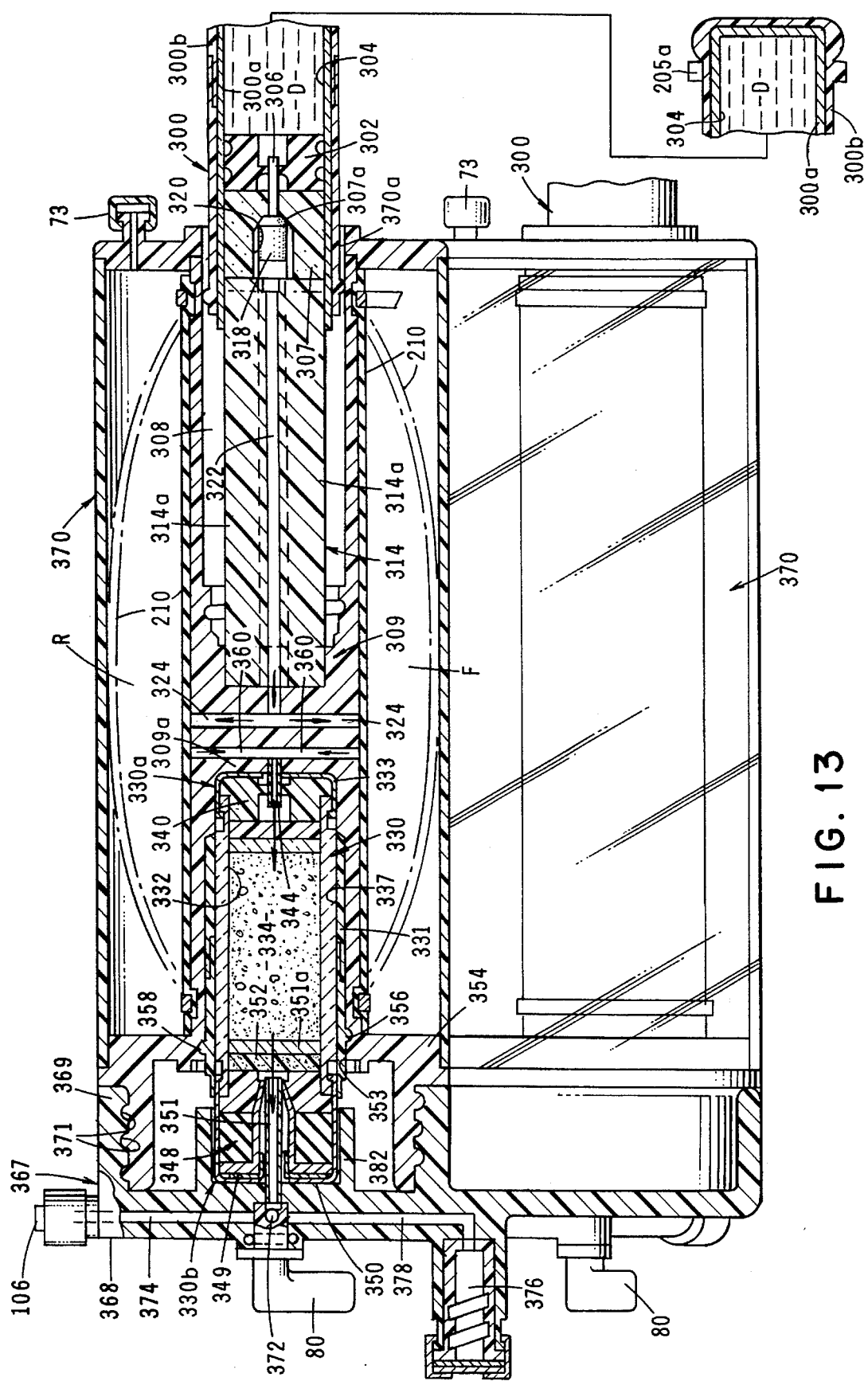
FIG. 13 is a cross-sectional view of the dispenser of FIG. 12 shown coupled with the manifold of the apparatus of the invention.

Referring now to FIGS. 12 and 13, yet another form of the invention is there shown. This form of the invention is similar in many respects to that shown in FIGS. 10 and 11 and like numerals are used to identify like components. More particularly, the fluid dispensers of this latest form of the invention are of similar construction to those shown in FIGS. 10 and 11, save that the additive assembly or adding means is disposed in the outlet portion of the dispenser and the inlet needle 241 has been replaced with an inlet valve means, the character of which will presently be described.

In this last embodiment of the invention, the diluent container assembly 300 which comprises a glass vial 300a and an overwrap 300b, is of similar construction to diluent container assembly 205, but the piston 302 which moves within reservoir 304 of the container 300a is pierceable by a blunt end cannula 306 which is molded into a valve housing 307 disposed within the inlet chamber 308 of the support means or support 309. The reservoir "R" of the dispenser is filled by urging container assembly 300 telescopically inwardly of chamber 308 causing cannula 306 to pierce piston 302 and causing the piston to move longitudinally of container reservoir 304. As container assembly 300 moves inwardly of chamber 308, it is guided by guide means shown here as a cross-like guide member 314 (FIG. 12) which is carried by longitudinally extending support 309. Guide member 314 includes four radially outwardly extending legs 314a the extremities of which guidingly engage the interior wall of container reservoir 304.

Fluid, such as diluent "D" flowing from reservoir 304 through cannula 306 will cause a valve member 318, which is carried within a chamber 320 provided in housing 307, to move to the left and away from valve seat 307a permitting fluid to flow toward reservoir "R" via a central passageway 322 provided in member 314. The fluid flowing through passageway 322 will flow under pressure through radially outwardly extending passageways 324 provided in support 309 and, as before, will cause elastomeric member 210 to distend outwardly in the manner shown by the phantom lines in FIG. 13.

As best seen in FIG. 13, in this latest form of the invention, the adding means is disposed proximate the outlet of the dispensing device and comprises a sealed cartridge assembly 330 having an additive-containing chamber 332 for containing an additive generally designated in FIG. 13 by the numeral 334. Once again, additive 334 can be of any material of the character defined in U.S. Ser. No. 08/053,723. By placing the adding means in the outlet portion of the dispensing device, an appropriate one of any number of different types of adding means or cartridge assemblies can be selected for use with the apparatus to affect the desired treatment protocol.

As indicated in FIG. 13, cartridge 330 is closely receivable within an outlet chamber 337 provided in support 309 and has first and second ends 330a and 330b. End 330a is sealably closed by a septum 340 which is held in place by a crimp cap 333 which exposes the septum so that it can be pierced by a hollow needle 344 which is mounted on a transverse wall 309a of support 309. End 330b of the cartridge is closed by a closure assembly 348 which includes a pierceable sleeve 349 that is pierceable by a delivery spike 351 carried by the base assembly or manifold of this embodiment of the invention. Closure assembly 348 is held in place by an annular crimp cap 350 which exposes sleeve 349. Sleeve 349 can be constructed from a pierceable material such as rubber, which can be punctured by delivery spike 351 to thereby open a fluid flow path which communicates with chamber 332 of the adding means via a glass frit 352 and porous distribution plug 352a.

In this latest form of the invention, cartridge assembly 330 is inserted into outlet chamber 337 through an opening 353 provided in end wall 354 of the dispenser and a thread 356, which is provided on a cartridge overpackage 330a, is mated with a thread 358 provided on support 309. As the cartridge assembly is threadably mated with the support, needle 344 will penetrate septum 340 establishing fluid communication between chamber 332 of the cartridge assembly and reservoir "R" via hollow needle 344 and passageways 360b provided in support 309.

In using the apparatus of this latest form of the invention, after container 300 has been filled with a suitable first component such as a diluent "D", piston 302 is inserted into the open end of the container and sealing cap 243 (FIG. 12) is emplaced over the assemblage thus formed so as to maintain the first component in a sterile, sealed condition until time of use.

Following the removal of tear-away cap 243 of the fluid container assembly 300, the container is inserted into the opening 359 provided in end wall 360a of dispenser assembly 360. As the container assembly is urged to the left as viewed in FIG. 13, cannula 306 will pierce plug 302 opening a fluid path between reservoir 304 and check valve chamber 320 of valve housing 307. Continued inward telescopic movement of the fluid container will cause the check valve to open permitting the diluent to flow to reservoir "R" via fluid passageways 322 and 324. As before, the overwrap 300b of container assembly 300 is externally threaded so that it can be locked inplace within chamber 308 in the manner previously described.

The mounting base assembly 367 of this latest form of the invention is of similar construction to that of the earlier described embodiments and includes a generally triangular planar base wall 368 similar to that shown in FIG. 6. Wall 368 is provided with a plurality of generally circular shaped, upstanding connector walls 370 each of which has internal threads 371. As before, the base wall 368 is also provided with first and second inlet passageways 372 and 374 which communicate with an outlet passageway 376 via a plurality of connector passageways 378.

Unique to the mounting base assembly of this latest form of the invention are delivery cannulas, shown here as delivery spikes 351, which are carried within upstanding socket-like cylindrical walls 382 provided on base wall 368. The delivery spikes are in communication with inlet passageways 372 and function to control the flow of fluid from the dispenser unit toward outlet passageway 376 of the mounting base assembly.

After each fluid dispenser is coupled with the base assembly in the manner previously described, fluid can be transferred to the mounting base assembly 367 and then to a patient or to a remote site via a transfer tube (not shown) which is appropriately connected to outlet connector 376. As before, the fluid transfer step is accomplished by first removing the protective caps 73 which cover the venting ports that are provided in each end wall and then, by selectively opening one or more of the mounting valve means or rotating control valves 80, which are mounted on base wall 368. As before, the control valves are disposed intermediate first and second inlet passageways 372 and 374 and outlet passageway 376 and function to control the flow of fluid toward the outlet passageway.

Upon opening a selected one of the control valves, the bladder 210 of the dispenser associated with that control valve will move toward its less distended, initial starting position thereby urging the fluid "F" contained within reservoir of that dispenser outwardly of the apparatus in the manner previously described.

Fluid can also be introduced into mounting base assembly via auxiliary septums 106 carried by the base assembly and in communication with second inlet passageways 374. By appropriate operation of control valves 80, fluid added via septums 106 can be intermixed with fluid flowing into the mounting base from the fluid dispensers or it can flow directly to outlet passageway 376 via connector passageways 378.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid dispensing apparatus comprising:

(a) a mounting base having first and second fluid inlets, a fluid outlet in communication with said fluid inlets, and valve means in communication with said fluid outlet for controlling fluid flow through said outlet; and (b) at least two fluid dispensing devices connected to said mounting base, each said device comprising:

(i) a housing having walls defining an internal chamber and support means for supporting a stored energy source within said internal chamber, said housing also having connection means for connecting said housing to said mounting base, said support means having an inlet chamber and an outlet chamber in communication with one of said first and second fluid inlets of said base; and (ii) filling means for introducing fluid into said inlet chamber of said support means;

(iii) a generally tubular shaped elastomeric member connected proximate its ends to said support means, said elastomeric member having a central portion distendable by fluid flowing into said inlet chamber of said support means from a first position in proximity with said support means to second position; and (iv) adding means disposed within said outlet chamber of said support means for adding an additive to fluid introduced into said inlet chamber by said filling means, said adding means comprising a container and an additive contained within said container.

2. An apparatus as defined in claim 1 in which said additive comprises a beneficial agent.

3. An apparatus as defined in claim 1 in which said additive comprises a biologically active material.

4. An apparatus as defined in claim 1 in which said container comprises a sealed cartridge assembly having an additive containing chamber for containing said additive.

5. An apparatus as defined in claim 4 in which said mounting base includes first and second delivery spikes in communication with said first and second fluid inlets respectively, and in which said sealed cartridge assembly has inlet and outlet ends, each said outlet end being closed by a septum adapted to be pierced by one of said delivery spikes.

6. An apparatus as defined in claim 5 in which said support means includes a hollow cannula in communication with said outlet chamber of said support means and in which said inlet end of said sealed cartridge assembly is closed by a septum adapted to be pierced by said hollow cannula.

7. A fluid dispensing apparatus comprising:

(a) a portable mounting base having:
  (i) a plurality of fluid inlet passageways; and
  (ii) a fluid outlet passageway in communication with said fluid inlet passageways; and (b) a plurality of fluid dispensing devices connected to said base, each said device comprising:
  (i) a housing having walls defining an internal chamber and an elongated support member for supporting a stored energy source within said internal chamber, said housing also having connection means for connecting said housing to said mounting base, said support member having a fluid inlet chamber having a fluid inlet and a fluid outlet chamber having a fluid outlet in communication with one of said first and second fluid inlet passageways of said base;
  (ii) filling means for introducing fluid into said fluid inlet chamber of said support member, said filling means comprising a fluid container telescopically receivable within said fluid inlet chamber of said support member;
  (iii) a generally tubular shaped elastomeric member connected proximate its ends to said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position; and
  (iv) adding means carried by said support means for adding an additive to fluid introduced by said filling means, said adding means comprising a container receivable within said outlet chamber of said support and an additive disposed within said container.

8. A fluid dispensing apparatus as defined in claim 7 in which said portable mounting base further includes base valve means for controlling fluid flow through said fluid outlet passageway of said base.

9. A fluid dispensing apparatus as defined in claim 7 in which each said container of adding means has first and second ends, said second end being closed by a pierceable septum and in which said mounting base further includes delivery cannulas in communication with said fluid inlet passageways of said portable base, said delivery cannulas being adapted to pierce said pierceable septums of each said container.

10. A fluid dispensing apparatus as defined in claim 7 in which said connection means comprises external threads and in which said portable mounting base comprises a base wall having internal threads matable with said external threads.

11. A fluid dispensing apparatus as defined in claim 7 in which said additive comprises a beneficial agent.

12. A fluid dispensing apparatus as defined in claim 7 in which said additive comprises a biologically active material.

13. A fluid dispensing apparatus as defined in claim 7 in which said additive comprises a drug.

14. A fluid dispensing apparatus as defined in claim 7 in which said additive comprises an extended release drug.

15. A fluid dispensing apparatus comprising:

(a) a portable mounting base having:
  (i) a plurality of fluid inlet passageways; and
  (ii) a fluid outlet passageway in communication with said fluid inlet passageways; and (b) a plurality of fluid dispensing devices connected to said base, each said device comprising:
  (i) a housing having walls defining an internal chamber and an elongated support member for supporting a stored energy source within said internal chamber, said housing also having connection means for connecting said housing to said mounting base, said support member having a fluid inlet chamber having a fluid inlet comprising a filling cannula and a fluid outlet chamber having a fluid outlet in communication with one of said inlet passageways of said base;
  (ii) filling means for introducing fluid into said fluid inlet chamber of said support member, said filling means comprising a fluid container telescopically receivable within said fluid inlet chamber of said support member, said fluid container being closed by a pierceable septum adapted to be pierced by said filling cannula;
  (iii) a generally tubular shaped elastomeric member connected proximate its ends to said support means, said elastomeric member having a central portion disposed within said internal chamber of said housing and overlaying said fluid inlet and said fluid outlet of said support means, said central portion of said elastomeric member being distendable by fluid flowing through said fluid inlet of said support means from a first position in proximity with said support means to second position; and
  (iv) adding means carried by said support means for adding an additive to fluid introduced by said filling means, said adding means comprising a container receivable within said outlet chamber of said support member and an additive disposed within said container said container having first and second ends closed by first and second pierceable septums respectively.

16. A fluid dispensing apparatus as defined in claim 15 in which said support member further includes valve means for controlling fluid flow through said filling cannula.

17. A fluid dispensing apparatus as defined in claim 15 in which said mounting base includes first and second fluid inlets and first and second delivery spikes in communication with said first and second fluid inlets respectively, said delivery spikes being adapted to pierce one of said first and second septums of said container.

* * * * *